United States Patent [19]

Meilland

[11] Patent Number: Plant 6,171

[45] Date of Patent: May 10, 1988

[54] ROSE PLANT—MEINOBROC VARIETY

[75] Inventor: Marie-Louise Meilland, Antibes, France

[73] Assignee: The Conard-Pyle Company, West Grove, Pa.

[21] Appl. No.: 833,611

[22] Filed: Feb. 27, 1986

[51] Int. Cl.[4] ..... A01H 5/00

[52] U.S. Cl. ..... Plt./20

[58] Field of Search ..... Plt./20

*Primary Examiner*—Robert E. Bagwill

*Attorney, Agent, or Firm*—Burns, Doane, Swecker & Mathis

[57] ABSTRACT

A new and distinct variety of Hybrid Tea rose plant is provided which forms elegant double red blossoms. The blossoms are vermilion red on the upper surface and cherry red on the under surface and are exceptionally attractive at the bud stage and at the beginning of the opening process. The plant exhibits a vigorous growth habit and is well suited for cut flower production under greenhouse conditions. Good resistance to fungus diseases is manifest.

1 Drawing Sheet

SUMMARY OF THE INVENTION

The new variety of Hybrid Tea rose plant was created by artificial pollination wherein two parents were crossed which previously had been studied in the hope that they would contribute the desired characteristics. The female parent (i.e., the seed parent) of the new variety was the variety Jacqueline (U.S. Plant Pat. No. 2,183). The male parent (i.e., the pollen parent) of the new variety was produced by crossing an unintroduced variety with pollen from the Jelvanica variety. The parentage of the new variety can be summarized as follows:

Jacqueline × (Unintroduced variety × Jelvanica).

The seeds resulting from the above pollination were sown in a greenhouse and 73 plantlets were obtained which were physically and biologically different from each other. Selective study resulted in the identification of a single plant of the new variety.

It was found that the new variety of Hybrid Tea rose plant of the present invention possesses the following combination of characteristics:

(a) forms elegant double red blossoms which are vermilion red on the upper surface and cherry red on the under surface,
(b) is particularly well suited for growing under greenhouse conditions,
(c) exhibits a vigorous growth habit, and
(d) exhibits good resistance to fungal diseases.

The new variety well meets the needs of the cut flower industry since the plant is strong and vigorous and grows well under greenhouse conditions.

The new variety has been found to undergo asexual propagation by a number of routes, including budding, winter bench grafting, etc. The characteristics of the new variety have been found to be strictly transmissible by such asexual propagation from one generation to another.

The new variety has been named the Meinobroc variety.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety were observed during January while grafted on *Rosa indica* understock and growing in a greenhouse at Cap d'Antibes, France.

DETAILED DESCRIPTION

Figures 1, 2, 3, 4, 5, 6, 7, 8, 9, 10, 11, 12, 13, 14, 15, 16, 17:
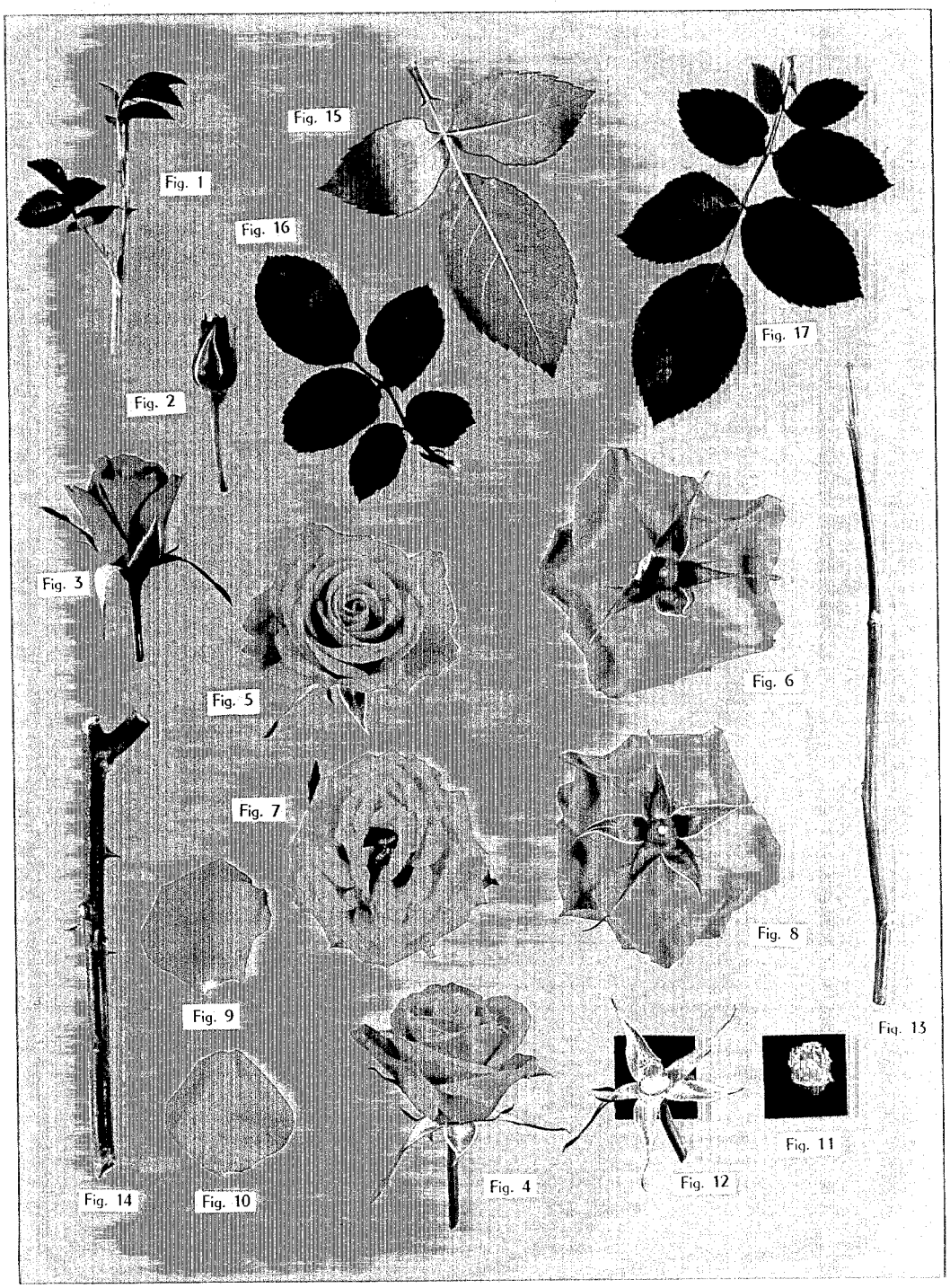
FIG. 1 illustrates a specimen of a young shoot.
FIG. 2 illustrates a specimen of a floral bud before the opening of the sepals.
FIG. 3 illustrates a specimen of a floral bud at the opening of the seapls.
FIG. 4 illustrates a specimen of a floral bud at the opening of the petals.
FIG. 5 illustrates a specimen of a fully open flower—plan view—obverse.
FIG. 6 illustrates a specimen of a fully open flower—plan view—reverse.
FIG. 7 illustrates a specimen of a fully open flower immediately prior to petal drop—plan view—obverse.
FIG. 8 illustrates a specimen of a fully open flower immediately prior to petal drop—plan view—reverse.
FIG. 9 illustrates a specimen of a petal—upper surface.
FIG. 10 illustrates a specimen of a petal—under surface.
FIG. 11 illustrates a specimen of a floral receptacle showing the arrangement of the stamens and pistils.
FIG. 12 illustrates a specimen of a floral receptacle showing the arrangement of the pistils (stamens removed)
FIG. 13 illustrates a specimen of a flowering stem.
FIG. 14 illustrates a specimen of a main branch.
FIG. 15 illustrates specimens of leaf with three leaflets—under surface.
FIG. 16 illustrates specimens of leaf with five leaflets—upper surface.
FIG. 17 illustrates a specimen of a leaf with seven leaflets—upper surface.

The chart used in the identification of the colors is that of The Royal Horticultural Society (R.H.S. Colour Chart). The description is based on observations made during January while grafted on *Rosa indica* understock and growing in a greenhouse at Cap d'Antibes, France.

Class: Hybrid tea.

Plant:

*Height.*—Plants which were pruned to a height of 85 cm. produced floral stems having a length of approximately 40 to 70 cm.

*Habit.*—Upright.

Branches:

*Color.*—Young stems: Yellow-Green Group 146B. Adult wood: Yellow-Green Group 146A.

Leaves:

*Petioles.*—Upper surface: noticeable veination, reddish-brown on young foilage, medium green on adult foliage. Under surface: smooth light green.

*Leaflets.*—Number 3, 5, and 7 (most often). Shape: elliptic. Serration: very simple and regular. Texture: tough. General appearance: ample and dense with a somewhat glossy surface. Color (young foliage): upper surface: reddish-brown. under surface: reddish-brown. Color (adult foliage): upper surface: dark green. Yellow-Green Group 147A, often with reddish serration. under surface: medium green, Yellow-Green Group 147B.

Inflorescence:

*Number of flowers.*—Generally one per stem.

*Peduncle.*—Straight and rigid, approximately 7 cm. on average.

*Buds.*—Shape: oblong. Length: approximately 3 cm. on average. Color upon opening: upper surface: carmine red, Red Group 46B. under surface: deep dull red, Red Group 46A, more or less suffused with black.

*Flower.*—Shape: sides are substantially parallel and petals are fully double. Diameter: approximately 10 cm. on average. Color (when opening begins): upper surface: deep vermilion red, Red Group 44A on external petals, and medium vermilion red, Red Group 44B on inner petals. under surface: deep dull red, Red Group 46A, slightly lighter on the inner petals. Color (when partially open): upper surface: bright vermilion red, Red Group 44B. under surface: dull cherry red, Red Group 45B. Color (at end of opening): upper surface: bright vermilion red, Red Group 44B. under surface: dull cherry red, Red Group 45B. Fragrance: slight. Lasting quality: long. Petal number: approximately 30 on average. Petal form: usually flat and slightly pointed at the tip, a few incomplete petals sometimes are present near the stamens. Stamen number: approximately 113 on average. Anthers: golden yellow with margins of fuschia.

Development:

*Disease resistance.*—Exhibits good resistance to major fungal diseases which commonly attack roses.

I claim:

1. A new and distinct variety of Hybrid Tea rose plant characterized by the following combination of characteristics:

(a) forms elegant double red blossoms which are vermilion red on the upper surface and cherry red on the under surface, (b) is particularly well suited for growing under greenhouse conditions, (c) exhibits a vigorous growth habit, and (d) exhibits good resistance to fungal diseases;

substantially as herein shown and described.

* * * * *